(12) United States Patent
Gulati et al.

(10) Patent No.: US 8,957,014 B2
(45) Date of Patent: *Feb. 17, 2015

(54) SENSITIZATION OF TUMOR CELLS TO RADIATION THERAPY THROUGH ADMINISTRATION OF ENDOTHELIN AGONISTS

(71) Applicants: The Board of Trustees of the University of Illinois, Urbana, IL (US); Spectrum Pharmaceuticals, Inc., Irvine, CA (US)

(72) Inventors: Anil Gulati, Naperville, IL (US); Guru Reddy, Irvine, CA (US); Luigi Lenaz, Newtown, PA (US)

(73) Assignees: Spectrum Pharmaceuticals, Inc., Irvine, CA (US); The Board of Trustees of the University of Illinoise, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/761,043

(22) Filed: Feb. 6, 2013

(65) Prior Publication Data

US 2013/0150649 A1  Jun. 13, 2013

Related U.S. Application Data

(63) Continuation of application No. 11/845,648, filed on Aug. 27, 2007, now Pat. No. 8,394,757, and a continuation of application No. 11/460,202, filed on Jul. 26, 2006, now Pat. No. 7,976,835, which is a continuation-in-part of application No. 10/691,915, filed on Oct. 23, 2003, now abandoned.

(60) Provisional application No. 60/824,197, filed on Aug. 31, 2006, provisional application No. 60/420,960, filed on Oct. 24, 2002.

(51) Int. Cl.

| A61K 38/00 | (2006.01) |
|---|---|
| A61N 5/00 | (2006.01) |
| A61K 41/00 | (2006.01) |
| A61K 31/00 | (2006.01) |
| A61K 31/28 | (2006.01) |
| A61K 31/337 | (2006.01) |
| A61K 31/4745 | (2006.01) |
| A61K 31/519 | (2006.01) |
| A61K 31/704 | (2006.01) |
| A61K 33/24 | (2006.01) |
| A61K 38/17 | (2006.01) |
| A61K 38/22 | (2006.01) |
| A61K 45/06 | (2006.01) |
| A61N 5/10 | (2006.01) |

(52) U.S. Cl.
CPC ............ *A61K 41/0038* (2013.01); *A61K 31/00* (2013.01); *A61K 31/28* (2013.01); *A61K 31/337* (2013.01); *A61K 31/4745* (2013.01); *A61K 31/519* (2013.01); *A61K 31/704* (2013.01); *A61K 33/24* (2013.01); *A61K 38/1703* (2013.01); *A61K 38/2285* (2013.01); *A61K 45/06* (2013.01); *A61N 5/00* (2013.01); *A61N 2005/1098* (2013.01)

USPC ............ 514/1.1; 514/16.1; 514/19.2; 378/65

(58) Field of Classification Search
None
See application file for complete search history.

(56) References Cited

U.S. PATENT DOCUMENTS

| 5,112,954 | A  | * | 5/1992  | Abrams et al. ............. 530/391.9 |
|---|---|---|---|---|
| 5,550,110 | A  |   | 8/1996  | Cody et al. |
| 5,612,359 | A  |   | 3/1997  | Murugesan |
| 5,811,416 | A  |   | 9/1998  | Chwalisz et al. |
| 6,469,058 | B1 |   | 10/2002 | Grove et al. |
| 7,976,835 | B2 |   | 7/2011  | Gulati |
| 8,026,216 | B2 |   | 9/2011  | Gulati |
| 8,030,278 | B2 |   | 10/2011 | Gulati |
| 8,217,010 | B2 |   | 7/2012  | Gulati |
| 8,349,802 | B2 |   | 1/2013  | Gulati |
| 8,394,757 | B2 |   | 3/2013  | Gulati |
| 8,440,620 | B2 |   | 5/2013  | Gulati |
| 2002/0082285 | A1 |   | 6/2002  | Lebwohl |
| 2003/0104976 | A1 |   | 6/2003  | Davar et al. |
| 2003/0229004 | A1 |   | 12/2003 | Zarling et al. |
| 2004/0138121 | A1 |   | 7/2004  | Gulati |
| 2007/0032422 | A1 |   | 2/2007  | Gulati |
| 2012/0245105 | A1 |   | 9/2012  | Gulati |
| 2013/0101552 | A1 |   | 4/2013  | Gulati |
| 2013/0102543 | A1 |   | 4/2013  | Gulati |

FOREIGN PATENT DOCUMENTS

| EP | 655463 | A1 | 5/1995 |
|---|---|---|---|
| EP | 815870 | A1 | 1/1998 |
| EP | 950418 | A2 | 10/1999 |
| WO | 96/19233 | A2 | 6/1996 |
| WO | 00/67024 | A1 | 11/2000 |
| WO | 01/00198 | A2 | 1/2001 |

(Continued)

OTHER PUBLICATIONS

Watakabe et al (Biochemical and Biophysical Research Communications, 1992, vol. 185, pp. 867-873).*
Battistini et al., Endothelins: A quantum leap forward. Drug News and Perspectives, vol. 8, No. 6, pp. 365-391 (1995).
Bell et al., A comparative study of tumour blood flow in modification in two rat tumour systems using endothelin-1 and angiotensin II: Influence of tumour size on angiotensin II response. Int. J. Cancer, 67(5) 730-8 (1996).
Bell et al., Effect of endothelin-1 and sarafotoxin, S6c on blood flow in a rat tumor. J. Cardiovasc. Pharmacol., vol. 26, Suppl 3, p. S222-S225 (1995).
Bell et al., Modification of blood flow in the HSN tumor and normal tissues of the rat by the endothelin Etb receptor agonist, IRL 1620. Int. J. Cancer, vol. 80, No. 2, pp. 295-302 (1999).

(Continued)

*Primary Examiner* — Karen Canella

(57) ABSTRACT

Methods to sensitize tumor cells to radiation therapy through the administration of an endothelin agonist such as the $ET_B$ agonist IRL1620.

12 Claims, 1 Drawing Sheet

(56) References Cited

FOREIGN PATENT DOCUMENTS

| WO | 01/91736 A2 | 12/2001 |
|---|---|---|
| WO | 03/009805 A2 | 2/2003 |
| WO | 03/045434 A2 | 6/2003 |
| WO | 03/070234 A1 | 8/2003 |
| WO | 2004/037235 A2 | 5/2004 |
| WO | 2006/057988 A2 | 6/2006 |
| WO | 2006/091767 A2 | 8/2006 |

OTHER PUBLICATIONS

Bell et al., Tumor blood flow modification by endothelin-related peptides in the rat HSN fibrosarcoma. British Journal of Cancer, 74, Suppl. 27, pp. S161-S163 (1996).

Bell et al., Vascular response of tumor and normal tissues to Endothelin-1 following antagonism of Eta and Etb receptors in anaesthtised rats. Int. J. Cancer, vol. 73, No. 2, pp. 283-289 (1997).

Bhalla et al., Potentiation of morphine analgesia by BQ123, an endothelin antagonist. Peptides, vol. 23, pp. 1837-1845 (2002).

Bhargava et al., Modification of brain and spinal cord dopamine D1 receptors labeled with [3H]SCH 23390 after morphine withdrawal from tolerant and physically dependent rats. The Journal of Pharmacology and Experimental Therapeutics, vol. 252, No. 3, pp. 901-907 (1990).

Calbiochem Catalog (1996/1997) p. 208.

Cemazar et al., the endothelin B (ETB) receptor agonist IRL 1620 is highly vasoconstrictive in two synergenic rat tumour lines: Potential for selective tumour blood flow modification. Bristish Journal of Cancer, vol. 93, No. 1, pp. 98-106 (2005).

Chaplin et al., Modification of tumor blood flow: current status and future directions. Seminars in Radiation Oncology, vol. 8, No. 3, pp. 151-163 (1998).

Davar et al., Behavioral signs of acute pain produced by application of endothelin-1 to rat sciatic nerve. NeuroReport, vol. 9, No. 10, pp. 2279-2283 (1998).

Davenport, International Union of Pharmacology. XXIX. Update on Endothelin receptor nomenclature. Pharmacological Revews, vol. 54, No. 2, pp. 219-226 (2002).

Del Bufalo et al., Endothelin-1 acts as a survival factor in ovarian carcinoma cells. Clinical Science, vol. 103, Suppl. 48, pp. 302S-305S (2002).

Duggan et al., Protection against aspirin-induced human gastric mucosal injury by bosentan, a new endothelin-1 receptor antagonist. Aliment Pharmacol. Ther., vol. 13, pp. 631-635 (1999).

Eisenberger, Chemotherapy in prostate cancer. Current Genitourinary Cancer Surgery, pp. 507-518 (1990).

Fabricio et al., Essential role for endothelin Etb receptors in fever induced by LPS (E. coli) in rats. British Journal of Pharmacology, vol. 125, pp. 542-548 (1998).

Filep et al., Effects of calcium antagonists on endothelin-1-induced myocardial ischaemia and oedema in the rat. British Journal of Pharmacol., vol. 118(4), pp. 893-900 (1996).

Gaidano et al., Lymphomas. Cancer Principles and Practice of Oncology, 5th Edition, 1997, p. 2198.

Griffin et al., Effect of a combination of mild-temperature hyperthermia and nicotinamide on the radiation response of experimental tumors. Radiation Research, vol. 153, No. 3, p. 327-331 (2000).

Hellman, Radiation Therapy. Cancer. Principles and Practice of Oncology, 5th Edition, 1997, p. 326.

Ishibashi et al., Growth of hepatocarcinoma and endothelian. Annual Research Report, Foundation for Growth Science, No. 19, p. 193-204 (1996).

Jarvis et al., ABT-627, an endothelin Eta receptor-selective antagonist, attenuates tactile allodynia in a diabetic rat model of neuropathic pain. European Journal of Pharmacology, vol. 388, pp. 29-35 (2000).

Jordan et al., Insulin increases the sensitivity of tumors to irradiation: involvement of an increase in tumor oxygenation mediated by nitric oxide-dependent decrease of the tumor cells oxygen consumption. Cancer Research, vol. 62, pp. 3555-3561 (2002).

Jordan et al., Potentiation of radiation-induced regrowth delay by isosorbide dinitrate in FSAII murine tumors. Int. J. Cancer, vol. 103, No. 1, pp. 138-141 (2003).

K. Parfitt (ED)., Analgesics Anti-inflammatory drugs and antipyretics. Martindale the complete drug reference (32nd Edition), Pharmaceutical Press, 1999.

Kikuchi et al., Decreased Etb receptor expression in human metastatic melanoma cells. Biochemical and Biophysical Research Communications, vol. 219, No. 3, pp. 734-739 (1996).

Kroodsma et al., Endothelins: possibly a new pharmacological starting point in cardiovascular disease, kidney disease and oncological conditions. Ned Tijdschr Geneeskd. vol. 141, No. 38, pp. 1806-1810 (1997).

Lahav et al., An endothelin receptor B antagonist inhibits growth and induces cell death in human melanoma cells in vitro and in vivo. Prcoeedings of the National Academy of Sciences of USA, vol. 96, pp. 11496-11500 (1999).

Lenaz et al., IRL-1620 increases the efficacy of radiation treatment in mice bearing lymphoma cell induced tumors. Blood, vol. 108 (11), Part 2, p. 269B (2006).

Martinive et al., Reversal of temporal and spatial heterogeneities in tumor perfusion identifies the tumor vascular tone as a tunable variable to improve drug delivery. Molecular Cancer Therapeutics, vol. 5 (6): 1620-1627 (2006).

Matsumaru et al., Bosentan, a novel synthetic mixed-type endothelin receptor antagonist, attenuates acute gastric mucosal lesions induced by indomethacin and HCI in the rat: Role of endogenous endothelin-1. Journal of Gastroenterology, vol. 32, pp. 164-170 (1997).

McQueen et al., Endothelin-1 activates ETA receptors to cause reflex scratching in BALB/c mice. British Journal of Pharmacoogy, 151, pp. 278-284 (2007).

Murata et al., Chronic vascular toxicity of doxorubicin in an organ-cultured artery. British Journal of Pharmacology, vol. 132, pp. 1365-1373 (2001).

Nelson et al., Endothelin-1 production and decreased endothelin B receptor expression in advanced prostate cancer. Cancer Research, vol. 56, No. 4, p. 663-668 (1996).

Nieder et al, The role of pentoxifylline as a modifier of radiation therapy. Cancer Treatment Reviews, vol. 31(6): 448-455 (2005).

NTC00613691 downloaded from the web at clinicaltrials.gov on Dec. 18, 2011, A phase I, open-pabel, ascending dose study of the safety, tolerability, pharmacokinetics and pharmacodynamics of the endothelin B agonist, SPI-1620, in patients with recurrent or progressive carcinoma.

Paclitaxel (TAXOL) insert, revised Jan. 2008, Bristol-Meyers Squibb Company.

Rai et al., Etb receptor agonist, IRL 1620, does not affect paclitaxel plasma pharmacokinetics in breast tumour bearing rats. Journal of Pharmacy and Pharmacology, vol. 57, No. 7, pp. 869-879 (2005).

Rai, et al., Evidence for the involvement of ETB receptors in ET-1-induced changes in blood flow to the rat breast tumor. Cancer Chemother. Pharmacol., vol. 51, No. 1, p. 21-28 (2003).

Rajeshkumar et al., Endothelin B receptor agonist, IRL 1620, enhances the anti-tumor efficacy of paclitaxel in breast tumor rats. Breast Cancer Research and Treatment, vol. 94, No. 3, p. 237-247 (2005).

Rajeshkumar et al., ETB receptor agonist, IRL-1620 enhances the efficacy of cyclophosphamide and cisplatin in ovarian tumor bearing mice. Proceedings of the American Association for Cancer Research, vol. 48, p. 961 (2007).

Rajeshkumar et al., IRL-1620, a tumor selective vasodilator, augments the uptake and efficacy of chemotherapeutic agents in prostate tumor rats. The Prostate, 67: 701-713 (2007).

Rajeshkumar et al., N-Suc-[Glu9, Ala11,15]ET-1(8-21) Increases blood perfusion and enchances paclitaxel delivery to the tumor. Proceeding of the Annual meeting of the American Association for Cancer Research, vol. 46, p. 5741 (2005).

Rowinsky et al, Paclitaxel (Taxol). Review Article in the New England Journal of Medicine, vol. 332, No. 15, pp. 1004-1014 (1995).

Seo et al., The interaction between two radiosensitizers: 5-iododeoxyuridine and caffeine. Cancer Research, vol. 66, No. 1, pp. 490-498 (2006).

(56) References Cited

OTHER PUBLICATIONS

Sonveaux et al., "Modulation of the tumor vasculature functionality by ionizing radiation accounts for tumor radiosensitization and promotes gene delivery", The FASEB Journal, vol. 16, No. 14, p. 1979-1981 (2002).

Sonveaux et al., Endothelin-1 is a critcal mediator of myogenic tone in tumor arterioles: implications for cancer treatment. Cancer Research, vol. 64(9): 3209-3214 (2004).

Takai et al., A potent and specific agonist, Suc-[Glu9, Ala11, 15]-Endothelin-1 (8-21), IRL 1620, for the ETB receptor. Biochemical and Biophysical Research Communications, vol. 184, No. 2, pp. 953-959 (1992).

Takita H., Effect of vasodilators in experimental solid tumor chemotherapy. Journal of Experimental and Clinical Cancer Research, vol. 2, No. 1, pp. 47-48 (1999).

TAXOL product label (Feb. 10, 2010).

University of Illinois at Chicago: List of Posters presentations in 2004 AAPS Annual Meeting (Baltimore), www2.uic.edu/std_orgs/prof/aaps/posters.htm, Online pp. 1-4.

Wu C., Recent discovery and development of endothelin receptor antagonists. Exp. Opin. Ther. Patents, 10(11), 1653-1668 (2000).

Wu-Wong et al., Extracellular signal-regulated kinases are involved in the antiapoptotic effect of endothelin-1. The Journal of Pharmacology and Experimental Therapeutics, vol. 293(2), pp. 514-521 (2000).

* cited by examiner

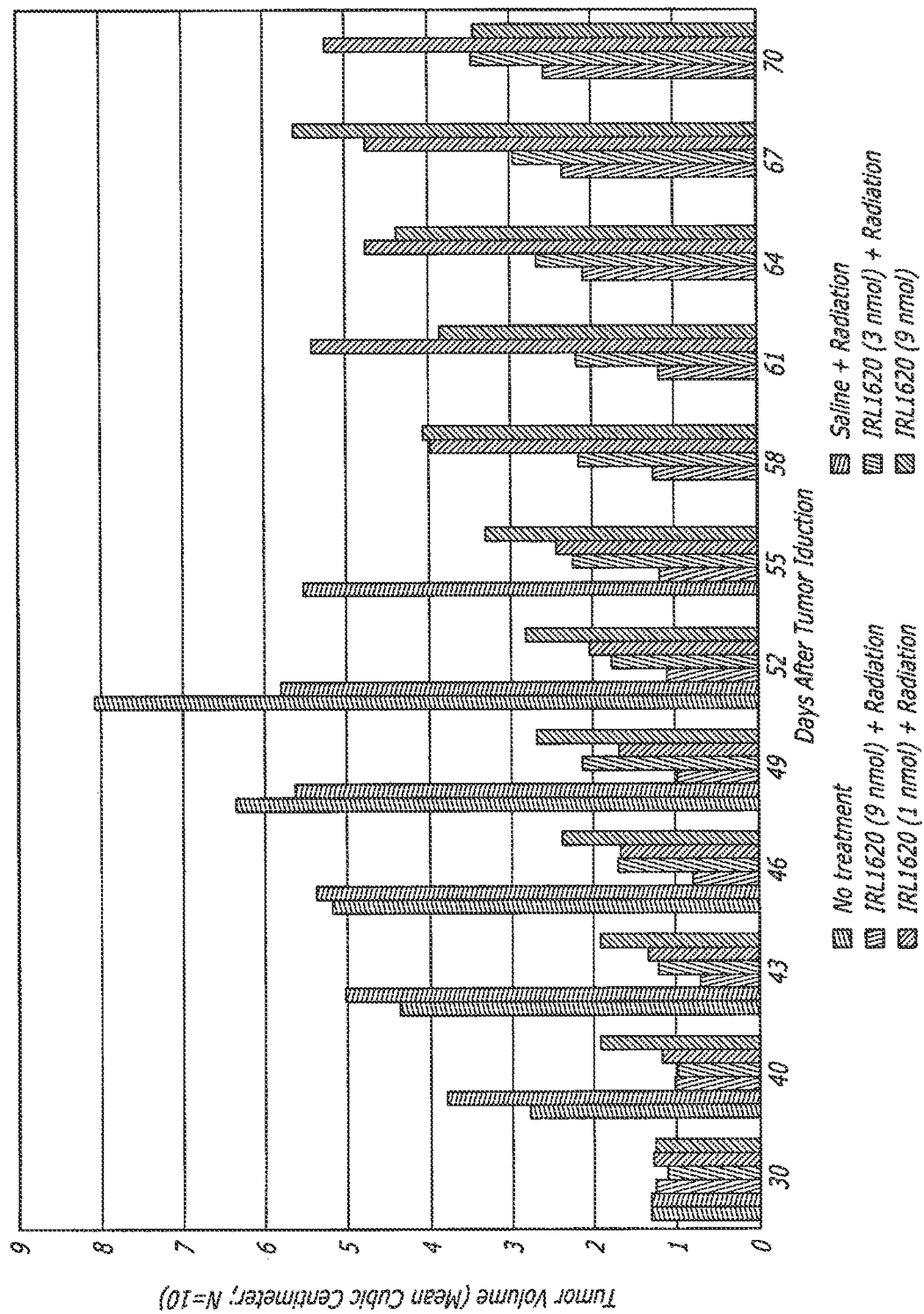

SENSITIZATION OF TUMOR CELLS TO RADIATION THERAPY THROUGH ADMINISTRATION OF ENDOTHELIN AGONISTS

CROSS REFERENCE TO RELATED APPLICATIONS

This application is a continuation of U.S. patent application Ser. No. 11/845,648, filed Aug. 27, 2007, Now U.S. Pat. No. 8,394,757 and claims benefit of the U.S. Provisional Application No. 60/824,197, filed Aug. 31, 2006. U.S. patent application Ser. No. 11/845,648 is a continuation-in-part of U.S. patent application Ser. No. 11/460,202, filed Jul. 26, 2006, now U.S. Pat. No. 7,976,835, which is a continuation-in-part of U.S. patent application 10/691,915, filed Oct. 23, 2003, now abandoned, which claims benefit of U.S. Provisional Patent Application No. 60/420,960, filed Oct. 24, 2002.

FIELD OF THE INVENTION

The present invention relates to the sensitization of tumor cells to radiation therapy through the administration of endothelin agonists. More specifically, the present invention relates to the sensitization of tumor cells to radiation therapy through the administration of IRL1620.

BACKGROUND OF THE INVENTION

Radiation therapy (irradiation) is an effective modality for the treatment of a variety of tumor types. Half of all cancer patients will receive radiation therapy during their course of treatment for cancer. Therefore, advances that increase the efficacy of radiation therapy would provide a great benefit. The present invention provides such an advance.

SUMMARY OF THE INVENTION

The present invention provides for the sensitization of tumor cells to radiation therapy through the administration of an endothelin agonist. Endothelin agonists provide this benefit by selectively increasing blood supply (and resulting oxygenation) to tumors thereby sensitizing the tumor cells to radiation therapy. Endothelin agonists can selectively increase blood flow to tumor cells through these compounds' interaction with the specialized vasculature of tumor tissue.

Specifically, one embodiment according to the present invention includes a method comprising sensitizing one or more tumors to radiation therapy by administering an endothelin agonist. In this embodiment, the endothelin agonist can be an endothelin B ($ET_B$) agonist. Another method according to the present invention comprises contributing to the treatment of cancer by administering an $ET_B$ agonist and a radiation therapy.

In certain embodiments, the endothelin agonist is administered to a patient in need thereof wherein the administering comprises systemic and/or local administration and the patient will receive at least two radiation therapies. In this embodiment, the administering of the endothelin agonist occurs in a manner selected from the group consisting of before all radiation therapies of the patient; before a subset of the radiation therapies of the patient; after all radiation therapies of the patient; after a subset of the radiation therapies of the patient; before and after all the radiation therapies of the patient; before all radiation therapies of the patient and after a subset of the radiation therapies of the patient; before a subset of the radiation therapies of the patient and after all radiation therapies of the patient; and before a subset of the radiation therapies of the patient and after a subset of the radiation therapies of the patient.

Endothelin agonists used in accordance with the present invention can include, without limitation, compounds selected from the group consisting of ET-1, ET-2, ET-3, BQ3020, IRL1620 (N-suc-[Glu$^9$, Ala$^{11,15}$]ET-1 (8-21)), sarafotoxin 56c, [Ala$^{1,3,11,15}$]ET-1, and combinations thereof. In certain embodiments the endothelin agonist will be an $ET_B$ agonist and will comprise IRL1620.

Endothelin agonists can be administered systemically and/or locally. Appropriate administration routes can include, without limitation, oral administration, intra-tumoral administration, intravenous administration, intravesical administration, intraarterial administration, intranasal administration and combinations thereof.

Another embodiment of the present invention includes a radiation combination therapy wherein a first radiation sensitizing compound and a second radiation sensitizing compound are co-administered and wherein the first radiation sensitizing compound enhances the effectiveness (increasing the sensitivity of a tumor cell to the cytototxic effects of radiation) of the second radiation sensitizer. Such embodiments may included, for example and without limitation an endothelin agonist wherein the endothelin agonist is an $ET_B$ agonist including, burt not limited to ET-1, ET-2, ET-3, BQ3020, IRL1620 (N-suc-[Glu$^9$, Ala$^{11,15}$]ET-1 (8-21)), sarafotoxin 56c, [Ala$^{1, 3, 11, 15}$]ET-1, and combinations thereof.

In another embodiment of the present the first and said second radiation sensitizers are synergistic and/or additive in their effects such that both the first and the second radiation sensitizer are more effective in sensitizing a tumor to the cytotoxic effects of radiation therapy than either first and said second radiation sensitizer used alone.

Embodiments according to the present invention also include compositions and articles of manufacture wherein compositions comprising at least one endothelin agonist are directed to be administered in a method described in the present disclosure.

Cancers treated in accordance with the present invention can include solid tumor or lymphomas. In certain embodiments, the treated cancer can include one or more of an ovarian tumor, a colon tumor, Kaposi's sarcoma, a breast tumor, a melanoma, a prostate tumor, a meningioma, a liver tumor, a breast phyllode tumor and combinations thereof.

BRIEF DESCRIPTION OF THE FIGURES

FIG. 1 shows the effect of the $ET_B$ agonist IRL1620 on the reduction in tumor volume induced by radiation therapy.

DETAILED DESCRIPTION

I. Definitions

Instructional Information: As used herein, the term "instructional information" shall mean material accompanying a pharmaceutical product that provides a description of how to administer the product. This instructional information generally is regarded as the "label" for a pharmaceutical product. Instructional information can come in many forms including, without limitation, a paper insert, c.d. rom or directions to a web site containing information relating to the pharmaceutical product.

Prodrug: As used herein, the term "prodrug" shall mean compounds that transform rapidly in vivo to a compound useful in the invention, for example, by hydrolysis. A thorough discussion of prodrugs is provided in Higuchi et al., Prodrugs as Novel Delivery Systems, Vol. 14, of the A.C.S.D. Symposium Series, and in Roche (ed.), Bioreversible Carriers in Drug Design, American Pharmaceutical Association and Pergamon Press, 1987.

Radiation Therapies: As used herein, the phrase "radiation therapies" shall mean radiation treatments administered to a patient that are separated by a period of time. The period of time separating the radiation therapies can be determined by a treating physician or veterinarian and can include, without limitation, minutes, hours, days, weeks, months or years. A given radiation therapy can be the same as or different from the radiation therapy immediately preceding or following it.

Sensitize and Sensitizing: As used herein, the terms "sensitize" or "sensitizing" shall mean making a tumor more susceptible to a treatment.

Treat, Treatment and Contributing to the Treatment Of: As used herein, the terms "treat", "treatment" and "contributing to the treatment of" shall mean preventing, retarding the progression or growth of, shrinking, or eliminating a cancer including a solid tumor or lymphoma. As such, these terms include both medical therapeutic and/or prophylactic administration, as appropriate.

The angioarchitecture of tumor blood vessels is different from that of normal blood vessels. Carmeliet & Jain, Nature, 407:249 (2000). Therefore, the vascular reactivity of tumors differs from that of normal tissue. For example, the administration of nitric oxide donors, nicotinamide and bradykinin agonists modulate blood flow to tumors. Jordan et al., Int J Radiat Oncol Biol Phys, 48:565 (2000); Fukumura et al., Am J Pathol, 150:713 (1997); Hirst et al., Br J Radiol, 67: 795 (1994). The present invention relates to the discovery that the unique angioarchitecture of tumor blood vessels allows endothelin agonists including $ET_B$ agonists to selectively increase blood supply to tumors and thereby sensitize the tumors to radiation therapy.

Endothelin is a vasoactive substance that modulates blood flow and is present in large concentrations in breast carcinoma tissues compared to normal breast tissue (specifically, endothelin can be present in an amount of about 12 pg/mg in breast carcinoma tissues as compared to about 0.12 pg/mg in normal breast tissue). Kojima et al., Surg Oncol, 4(6):309 (1995); Kurbel et al., Med Hypotheses, 52(4):329 (1999); Patel et al., Mol Cell Endocrinol, 126(2):143 (1997); Yamashita et al., Cancer Res, 52(14):4046 (1992); Yamashita et al., Res Commun Chem Pathol Pharmacol, 74(3):363 (1991). Endothelins are a family of cyclic peptides with 21 amino acids, comprising three isoforms in mammals, ET-1, ET-2 and ET-3. Inoue et al., Proc Natl Acad Sci USA 86:2863 (1989); Yanagisawa et al., Nature, 332:411 (1988). Endothelins exert their effects by binding to two distinct cell surface receptors, $ET_A$ and $ET_B$. The $ET_B$ receptor binds the three peptide isotypes with equal affinity. In contrast, the $ET_A$ receptor binds ET-1 with higher affinity than the other isoforms. Both receptors belong to the G protein-coupled receptor system and mediate biological responses from a variety of stimuli, including growth factors, vasoactive polypeptides, neurotransmitters and hormones. Masaki, J Cardiovasc Pharmacol, 35:S3 (2000); Gulati, Preface. Adv Drug Deliv Rev, 40:129 (2000); Gulati et al., Am J Physiol, 273:H827 (1997); Levin, N Engl J Med, 333:356 (1995). $ET_B$ receptors, a focus of the present invention, are present on both endothelial cells (ECs) and vascular smooth muscle cells (VSMCs) and are increased in breast cancer tissue (including in invasive as well as in ductal and lobular breast carcinoma tissue in humans) when compared to normal breast tissue. Wulfing et al., Oncol Rep, 11:791 (2004); Wulfing et al., Clin Cancer Res, 9:4125 (2003); Alanen et al., Histopathology, 36(2):161 (2000). Endothelin acts on $ET_B$ receptors to produce vascular dilation and increase blood flow to breast tumor tissue. $ET_B$ receptors predominating on ECs, produce vasodilatation via the release of factors such as prostacyclin and nitric oxide. de Nucci et al., Proc Natl Acad Sci USA, 85:9797 (1988). Because ET-1 produces an increase in blood flow to tumors by stimulating $ET_B$ receptors, an $ET_B$ receptor agonist can be used to selectively increase blood supply to tumors, thus increasing oxygenation of the tumors and sensitizing them to the effects of radiation therapy.

$ET_B$ receptors have been shown in, for example and without limitation, ovarian cancers, myofibroblasts, Kaposi's sarcoma tumor and intratumoral vessels, breast cancers and melanomas. Bagnato et al., Am J Pathol, 158:841 (2001); Alanen et al., Histopathology, 36(2):161 (2000); Bagnato et al., Cancer Res, 59:720 (1999); Kikuchi et al., Biochem Biophys Res Comm, 219:734 (1996). Therefore, administration of an $ET_B$ receptor agonist in combination with a radiation therapy can be used to contribute to the treatment of solid tumor or lymphomas, including, without limitation, ovarian cancer, colon carcinoma, Kapoli's sarcoma, breast cancer, and melanomas.

$ET_B$ agonists useful in accordance with the present invention include, without limitation, ET-1, ET-2, ET-3, BQ3020, IRL1620 (N-suc-[Glu$^9$, Ala$^{11,15}$]ET-1 (8-21)), sarafotoxin 56c, [Ala$^{1,3,11,15}$]ET-1, and combinations thereof. [Ala$^{1, 3, 11, 15}$]ET-1 is a linear analog of ET-1 in which the disulfide bridges have been removed by substitution of Ala for Cys residues. Saeki et al., Biochem Biophys Res Commun, 179:286 (1991). BQ3020 and IRL1620 are truncated linear synthetic analogs of ET-1 and are the most widely used selective synthetic agonists. IRL1620 is a linear ET-analog whose structure is based on the carboxy terminal end of ET-1 and has 120,000 fold selectivity for the $ET_B$ receptors. Okada & Nishikibe, Cardiovasc Drug Rev, 20:53 (2002); Douglas et al., Br J Pharmacol, 114:1529 (1995). IRL1620 is a highly selective and potent $ET_B$ agonist, with evidence being reported of its selectivity for the $ET_{B1}$ receptor subtype in preference over the $ET_{B2}$ subtype. Brooks et al., J Cardiovasc Pharmacol, 26 Suppl 3:S322 (1995).

In one embodiment of the present invention, an endothelin agonist is used in conjunction with a radiation therapy to contribute to the treatment of a solid tumor or lymphoma. In this method, the endothelin agonist, notably an $ET_B$ agonist, increases blood flow to the tumor, which is rich in $ET_B$ receptors.

As previously suggested, it is theorized, but not relied upon herein, that endothelin agonists stimulate $ET_B$ receptors to dilate tumor blood vessels, thereby increasing blood flow to the tumor. The increased blood perfusion of tumors caused by $ET_B$ agonists increases oxygenation of the tissue, enhancing the therapeutic action of radiation therapies.

EXAMPLE 1

Effect of IRL1620 on Tumor Radiation Therapy

As shown in the previously described example, endothelin selectively and transitionally increases blood flow to tumors producing increased oxygenation of the tumor. As oxygenation increases, so can radiation-induced cellular damage. Thus, the following described study was conducted to determine if IRL1620, an ETB agonist can increase the sensitivity of tumors to radiation therapy.

Inbred male Swiss albino mice (25 g) were used as subjects. Tumors were induced with Dalton's Lymphoma Ascites cells (1 million cells per animal). After 30 days, tumor volume was determined and animals with tumor sizes of about 1 cm³ or greater were included in the study. Animals were divided into six groups (10 animals per group) and were treated as described below every other day for five doses:

Group I: No treatment

Group II: 5 doses of saline on every alternate day via the tail vein plus radiation (4 Gy/dose) given 15 minutes after each dose of saline;

Group III: 5 doses of IRL1620 (9 nmol/kg) on every alternate day via the tail vein plus radiation (4 Gy/dose) given 15 minutes after each dose of IRL1620;

Group IV: 5 doses of IRL1620 (3 nmol/kg) on every alternate day via the tail vein plus radiation (4 Gy/dose) given 15 minutes after each dose of IRL1620;

Group V: 5 doses of IRL1620 (1 nmol/kg) on every alternate day via the tail vein plus radiation (4 Gy/dose) given 15 minutes after each dose of IRL1620; and Group VI: 5 doses of IRL1620 (9 nmol/kg) on every alternate day via the tail vein.

During radiation mice were shielded with lead except for a 3 cm diameter circular field where the tumor was centered. Tumor volume measurements occurred on days 40, 43, 46, 49, 52, 55, 58, 61, 64, 67 and 70 after tumor induction. Tumor diameter was measured using a digital caliper and tumor volume was calculated using the formula:

$V = \pi r_1^2 r_2$ where $r_1$ and $r_2$ are two perpendicular radii at the widest and longest regions of the tumor.

Survival of the animals was also documented.

As can be seen in FIG. 1, there was a significant increase in tumor volume in control animals and all control animals died by 53 days after tumor induction. Radiation alone did not significantly reduce tumor volume when compared to controls and there was no significant increase in survival. All radiation alone animals died by 56 days after tumor induction.

Animals treated with radiation 15 minutes after administration of 9 nmol/kg IRL1620 showed a significant reduction in tumor volume with a significant increase in life span. Only 4 out of 10 animals in this group died by 70 days after tumor induction. Animals treated with 9 nmol/kg IRL1620 alone produced a decrease in the development of tumor volume initially even though it was not as significant as animals treated with radiation 15 minutes after administration of 9 nmol/kg IRL1620. It was found that in this group 6 out of 10 animals died by 70 days after tumor induction. Animals treated with radiation 15 minutes after administration of 3 nmol/kg IRL1620 delayed the development of tumors. It was found that 7 out of 10 animals died by 70 days after tumor induction. Animals treated with radiation 15 minutes after administration of 1 nmol/kg IRL1620 along with radiation delayed tumor development. It was found that in this group 9 out of 10 animals died by 70 days after tumor induction. This study demonstrates that $ET_B$ agonists such as IRL1620 can be used as tumor radiation sensitizers.

In conclusion, endothelin agonists including the $ET_B$ agonist IRL1620 can be used as tumor-selective vasodilators and can be used to increase the efficacy of radiation therapy.

Pharmaceutical compositions containing the active ingredients are suitable for administration to humans or other mammals. Typically, the pharmaceutical compositions are sterile, and contain no toxic, carcinogenic, or mutagenic compounds that would cause an adverse reaction when administered. Administration of the pharmaceutical composition can be performed before, during, or after the onset of solid tumor or lymphoma growth.

A method of the present invention can be accomplished using active ingredients as described above, or as a physiologically acceptable salt, derivative, prodrug, or solvate thereof. The active ingredients can be administered as the neat compound, or as a pharmaceutical composition containing either or both entities.

The pharmaceutical compositions include those wherein the active ingredients are administered in an effective amount to achieve their intended purpose. More specifically, a "therapeutically effective amount" means an amount effective to prevent development of, to eliminate, to retard the progression of, or to reduce the size of a solid tumor or lymphoma. Determination of a therapeutically effective amount is well within the capability of those skilled in the art, especially in light of the detailed disclosure provided herein.

A "therapeutically effective dose" refers to that amount of the active ingredients that results in achieving the desired effect. Toxicity and therapeutic efficacy of such active ingredients can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained can be used in formulating a range of dosage for use in humans. The dosage of the active ingredients preferably lies within a range of circulating concentrations that include the $ED_{50}$ with little or no toxicity. The dosage can vary within this range depending upon the dosage form employed, and the route of administration utilized.

The exact formulation and dosage is determined by an individual physician in view of the patient's condition. Dosage amount and interval can be adjusted individually to provide levels of the active ingredients that are sufficient to maintain therapeutic or prophylactic effects.

The amount of pharmaceutical composition administered can be dependent on the subject being treated, on the subject's weight, the severity of the affliction, the manner of administration, and the judgment of the prescribing physician.

The active ingredients can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active ingredients into preparations which can be used pharmaceutically.

When a therapeutically effective amount of the active ingredients is administered, the composition can be in the form of a pyrogen-free, parenterally acceptable aqueous solution. The preparation of such parenterally acceptable solutions, having due regard to pH, isotonicity, stability, and the like, is within the skill in the art. A preferred composition for intravenous injection typically will contain an isotonic vehicle although this characteristic is not required.

For veterinary use, the active ingredients are administered as a suitably acceptable formulation in accordance with normal veterinary practice. The veterinarian can readily determine the dosing regimen that is most appropriate for a particular animal.

Administration routes can include systemic or local routes and can include, without limitation, oral administration, intra-tumoral administration, intravenous administration, intravesical administration, intraarterial administration, intranasal administration, and combinations thereof.

In certain embodiments, the endothelin agonist is administered to a patient in need thereof wherein the administering comprises systemic and/or local administration and the patient will receive at least two radiation therapies. In this embodiment, the administering of the endothelin agonist occurs in a manner selected from the group consisting of before all radiation therapies of the patient; before a subset of the radiation therapies of the patient; after all radiation therapies of the patient; after a subset of the radiation therapies of the patient; before and after all the radiation therapies of the patient; before all radiation therapies of the patient and after a subset of the radiation therapies of the patient; before a subset of the radiation therapies of the patient and after all radiation therapies of the patient; and before a subset of the radiation therapies of the patient and after a subset of the radiation therapies of the patient.

Radiation dosages and schedules used in accordance with the present invention can vary depending on the organ to be treated. Generally, appropriate dosages will range from about 1 to about 300 grey/dose. Total dosages can vary from about 200 to about 5000 grey. Schedules used in accordance with the present invention can also vary. In certain embodiments, a particular schedule can comprise daily treatments about 5 times per week for about six to about seven weeks or can comprise about twice daily treatments for about two to about three weeks. Particular dosages and schedules, however, will vary depending on the needs of particular patients and these provided examples should not be read as limiting the scope of the present invention. Finally, it should be noted that endothelin agonists including, without limitation, IRL1620, can also be used to enhance radiation enhancers. When used in this capacity, the endothelin agonists and radiation therapies can be administered according to all treatment embodiments previously described herein as if individually described.

Various adaptations and modifications of the embodiments can be made and used without departing from the scope and spirit of the present invention which can be practiced other than as specifically described herein. The above description is intended to be illustrative, and not restrictive. The scope of the present invention is to be determined only by the claims.

The terms and expressions which have been employed herein are used as terms of description and not of limitation, and there is no intention in the use of such terms and expressions of excluding equivalents of the features shown and described, or portions thereof, it being recognized that various modifications are possible within the scope of the present invention claimed. Moreover, any one or more features of any embodiment of the present invention can be combined with any one or more other features of any other embodiment of the present invention, without departing from the scope of the present invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the present invention otherwise claimed. No language in the specification should be construed as indicating any non-claimed element essential to the practice of the present invention.

Groupings of alternative elements or embodiments of the present invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

The invention claimed is:

1. A radiation combination therapy contributing to the treatment of a lymphoma in a patient in need thereof, the therapy comprising administering a first radiation sensitizing compound and a second radiation sensitizing compound to the patient, wherein administration of the first radiation sensitizing compound increases oxygenation of the lymphoma, thereby sensitizing the lymphoma to radiation-induced cellular damage, and wherein the first radiation sensitizing compound is an endothelin B ($ET_B$) receptor agonist; and administering a radiation to the patient, wherein administration of the radiation induces cellular damage to the lymphoma, thereby treating the lymphoma in the patient;

wherein administration of the first and the second radiation sensitizing compounds occurs before administration of the radiation to the patient.

2. The radiation combination therapy according to claim 1, wherein the $ET_B$ receptor agonist includes ET-1, ET-2, ET-3, BQ3020, IRL1620, sarafotoxin S6c, or [Ala$^{1,3,11,15}$]ET-1, or combinations thereof.

3. The radiation combination therapy according to claim 2, wherein the $ET_B$ receptor agonist is an IRL1620.

4. The radiation combination therapy according to claim 1, wherein the second radiation sensitizing compound includes metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine, 5-iododeoxyuridine, bromodeoxycytidine, fluorodeoxyuridine, hydroxyurea, or cisplatin, or mixtures thereof.

5. The radiation combination therapy according to claim 1, wherein administration of the first and the second radiation sensitizing compounds comprises systemic or local administration.

6. The radiation combination therapy according to claim 1, wherein administration of the first and the second radiation sensitizing compounds occurs through a route selected from the group consisting of oral administration, intra-tumoral administration, intravenous administration, intravesical administration, intraarterial administration, intranasal administration, and a combination thereof.

7. A radiation combination therapy for sensitizing a lymphoma to a radiation therapy in a patient in need thereof, the therapy comprising administering a first radiation sensitizing compound and a second radiation sensitizing compound to the patient, wherein administration of the first radiation sensitizing compound increases oxygenation of the lymphoma, thereby sensitizing the lymphoma to radiation-induced cellular damage, and wherein the first radiation sensitizing compound is an endothelin B ($ET_B$) receptor agonist; and administering a radiation to the patient, wherein administration of the radiation induces cellular damage to the lymphoma, thereby treating the lymphoma in the patient;

wherein administration of the first and the second radiation sensitizing compounds occurs before administration of the radiation to the patient.

8. The radiation combination therapy according to claim 7, wherein the $ET_B$ receptor agonist includes ET-1, ET-2, ET-3, BQ3020, IRL1620, sarafotoxin S6c, or [Ala$^{1,3,11,15}$]ET-1, or combinations thereof.

9. The radiation combination therapy according to claim 8, wherein the $ET_B$ receptor agonist is an IRL1620.

10. The radiation combination therapy according to claim 7, wherein the second radiation sensitizing compound includes metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine, 5-iododeoxyuridine, bromodeoxycytidine, fluorodeoxyuridine, hydroxyurea, or cisplatin, or mixtures thereof.

11. The radiation combination therapy according to claim 7, wherein administration of the first and the second radiation sensitizing compounds comprises systemic or local administration.

12. The radiation combination therapy according to claim 7, wherein administration of the first and the second radiation sensitizing compounds occurs through a route selected from the group consisting of oral administration, intra-tumoral administration, intravenous administration, intravesical administration, intraarterial administration, intranasal administration, and a combination thereof.

* * * * *